United States Patent [19]
Farchone

[11] Patent Number: 5,423,205
[45] Date of Patent: Jun. 13, 1995

[54] DENSITOMETER

[75] Inventor: Donald D. Farchone, Lakewood, Colo.

[73] Assignee: The Western Company of North America, Houston, Tex.

[21] Appl. No.: 896,441

[22] Filed: Jun. 10, 1992

[51] Int. Cl.[6] ............................................. G01N 4/00
[52] U.S. Cl. ............................. 73/32 R; 73/861.04; 166/280; 364/506
[58] Field of Search ............... 73/32 R, 61.41, 53.01, 73/61.71, 61.73, 195, 196, 861.04; 166/250, 280, 308; 364/502, 506, 558, 469, 550, 172

[56] References Cited

U.S. PATENT DOCUMENTS

| | | | |
|---|---|---|---|
| 3,657,532 | 4/1972 | Zimmerman | 250/43.5 |
| 3,958,447 | 5/1976 | Baker et al. | 73/32 R |
| 4,010,645 | 3/1977 | Herzi | 73/32 R |
| 4,341,107 | 7/1982 | Blair et al. | 73/3 |
| 4,390,957 | 6/1983 | Skarlos et al. | 73/61.41 |
| 4,494,209 | 1/1985 | Agarwal | 364/502 |
| 4,618,939 | 10/1986 | Davis | 364/555 |
| 4,654,802 | 3/1987 | Davis | 364/502 |
| 4,779,186 | 10/1988 | Handke et al. | 364/172 |
| 4,930,576 | 6/1990 | Berryman et al. | 166/308 |
| 5,023,819 | 6/1991 | Pitts | 364/558 |

FOREIGN PATENT DOCUMENTS

| | | | |
|---|---|---|---|
| 60-198414 | 10/1985 | Japan | G01F 1/74 |
| 528735 | 3/1939 | United Kingdom . | |
| 2073454 | 10/1981 | United Kingdom . | |

*Primary Examiner*—Hezron E. Williams
*Assistant Examiner*—Helen C. Kwok
*Attorney, Agent, or Firm*—Peter A. Bielinski

[57] ABSTRACT

An apparatus and method are provided for determining the relative density of a flowing fluid based upon the ratio of the fluid's flow rate before and after a material is added. Using analog or digital components, two signals are generated, representing the two flow rates, a first ratio of the two signals is derived, the ratio is compared to a constant, a second ratio of a second constant to the first ratio is derived, and the result of the comparing step is multiplied by the second ratio to generate a density signal representative of the relative density of the fluid after the material has been added.

38 Claims, 4 Drawing Sheets

DENSITOMETER

TECHNICAL FIELD OF THE INVENTION

This invention relates generally to the measurement of the density of a flowing fluid after material has been added to the fluid and, more particularly, to a method and apparatus for determining the relative density of the flowing fluid based upon the ratio of the fluid's flow rate before material is added to the flow rate after the material is added.

BACKGROUND OF THE INVENTION

One of the services provided in the oil field service industry pertains to the stimulation of an oil or gas bearing formation after a well hole has been drilled. Upper and lower plugs or packers are inserted in the well above and below perforations in the well casing, which provide access to the subsurface formation. A fracturing fluid is pumped into the well between the two packers and is forced, under high pressure, through the casing perforations into the formation. It is intended that the fluid will cause the formation to fracture outwardly from the perforations, providing channels for the oil or gas to flow into the well.

Once fractures have opened, a proppant is added to the fracturing fluid to be injected into the fractures. The proppant, which can be sand, bauxite, or other like material, props open the fractures to prevent them from closing when pumping of the fracturing fluid ceases and the pressure on the fractures is reduced. It can be appreciated that too little proppant may allow the fractures to close, thereby reducing the flow of oil or gas into the well. It can also be appreciated that too much proppant can clog the fractures, as well as the bore hole, fluid lines, pumps and valves, thereby also adversely affecting production and increasing the required maintenance.

To produce proppant-laden fracturing fluid (slurry), a "clean" base fluid is continuously pumped into a blending tank and a proppant is continuously added. Proppant-laden slurry is discharged from the blender and is pumped under high pressure through a pipe or flow line into the well. The amount of proppant added must be carefully monitored and controlled to ensure that production of the well is optimized.

One common device used to monitor the amount of proppant which has been added to the base fluid is a nuclear densitometer (or "densometer") which measures the density of the slurry being discharged from the blender. A radiation source, such as Cesium 137, is positioned against one side of the discharge flow line and a radiation detector is positioned against the opposite side. The radiation is directed through the first side of the flow line, through the discharged fluid, and through the opposite side of the flow line to the detector. The amount of radiation which actually reaches the detector is proportional to the density of the fluid: if the relative amounts of all other components in the slurry remain constant, the greater the density of the slurry (i.e., the more proppant in the slurry), the more radiation will be absorbed in the slurry and the less will be detected. The output signal from the detector can be processed and the density, in units such as pounds of sand added per gallon fluid (PSA), specific gravity units (SGU), or pounds per gallon (PPG) can be displayed for the operators.

A nuclear densitometer has many attendant disadvantages, one of which is its reliance upon a radiation source. It is necessary for the operator to have federal and, possibly, state licenses and be subject to extensive regulations. Handling and transportation of the device, while not dangerous, is subject to prescribed procedures. Additionally, as can be appreciated, the radiation source irradiates a portion of the fluid flow line to which the densitometer is attached, causing it to become radioactive. Consequently, that portion of the flow line must be handled and transported with as much care as the nuclear densitometer itself.

Other operational disadvantages include the need for separate units for different-size flow lines. Less radiation will be detected through an 8-inch flow line than through a 6-inch flow line, even if the density of the fluid is the same. Consequently, a different densitometer unit is usually used. Additionally, component age, temperature variations, and the decay of the radioactive source tend to cause the device to "drift." Consequently, various compensation techniques must be employed to prevent such drifting from being interpreted as increased or decreased fluid density. Finally, circuitry associated with a nuclear densitometer may be noisy and slow, resulting in inaccuracies and delays in the monitoring and control of the amount of proppant being added.

Consequently, a need has arisen for an apparatus and method for determining the amount of material added to a flowing fluid which substantially reduce or avoid the foregoing disadvantages.

SUMMARY OF THE INVENTION

In accordance with the present invention, an apparatus and method are provided for determining the relative density of a flowing fluid. The apparatus comprises an input stage for generating two flow signals representative of volumetric flow rates of a fluid flowing through two sections of a flow line, a calculating stage for generating a density signal representative of the relative density of the fluid flowing through the second stage of the flow line, and an output stage for displaying the density signal or otherwise making it available to an operator. The method comprises the steps of generating two signals representative of the flow rates of the fluid flowing through the two sections of flow line, deriving a ratio of the two signals, comparing the ratio to a first predetermined constant, deriving a second ratio of a second predetermined constant to the first ratio, and multiplying the result of the comparing step times the second ratio to generate an output density signal representative of the relative density of the fluid flowing through the second section of flow line (i.e., after material, such as proppant, has been added to the fluid).

In a specific embodiment, the input stage of the apparatus includes two inputs for receiving signals from suction and discharge flow rate sensors, each input signal having a frequency representative of the respective flow rate, and two outputs for providing two voltage signals proportional to the two frequencies. The calculating stage includes a first dividing means for providing the first ratio signal representative of the one voltage signal divided by the other, a comparing means for providing a difference signal representative of the difference between the first ratio signal and a first reference signal, a second dividing means for providing a second ratio signal representative of a second reference signal divided by the first ratio signal, and a multiplying means for providing a density signal substantially equal to the product of the difference signal times the second ratio signal and representing the amount of proppant in the fracturing fluid.

The present invention advantageously uses signals from flow rate sensors already in place and is sufficiently flexible to provide direct read-out of the relative density in any of several commonly-used units. Because the present invention relies upon a ratio of two input signals, different turbine sizes can be used without having to recalibrate the apparatus or use an entirely different unit. The method can be employed in conjunction with either an analog or a digital apparatus and can be incorporated into a feedback loop to monitor and quickly control the amount of proppant being added to the base fluid. The present invention does not employ a nuclear radiation source, and thus it does not have the attendant disadvantages thereof. Furthermore, the present invention is relatively fast, has reduced susceptibility to noise, and retains its accuracy despite temperature fluctuations and component aging.

DETAILED DESCRIPTION

Figure 1:
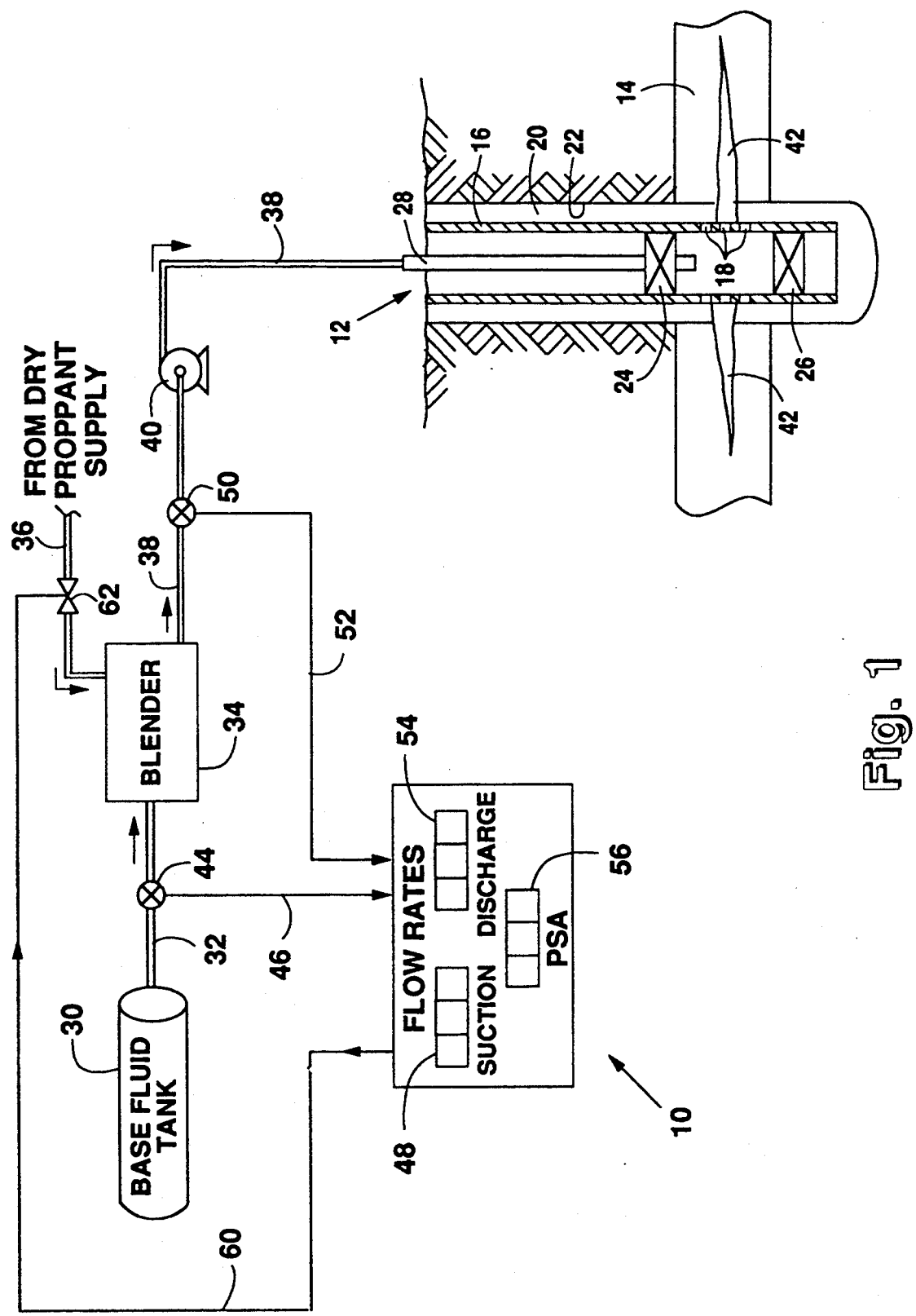
FIG. 1 schematically illustrates one embodiment of the present invention in use during a fracturing job.

FIG. 1 schematically illustrates an embodiment of the present invention 10 in use during a fracturing job. For clarity, unrelated pipes, valves and other equipment are not included in FIG. 1. A well 12 has been bored into a subsurface oil- or gas-bearing formation 14 and a well casing 16 with perforations 18 has been set in concrete 20 within the well bore 22. Perforations 18 through the casing 16 and concrete 18 provide access to the formation 14. Upper and lower packers 24 and 26, respectively, are positioned within the casing 16 above and below the perforations 18 to seal off the intermediate area. A tubing string 28 from the surface penetrates the upper packer 24 into the isolated area between the packers 24 and 26.

Base fluid from a storage device or tank 30 flows through a suction flow line 32 into a blender 34. Proppant from a dry proppant supply (not shown) flows through a supply line 36 into the blender 34. Other materials, such as gel setting agents and fluid loss control agents, can also be added to the fluid to form the fracturing fluid or slurry. Blended fracturing fluid then flows from the blender 34 through a discharge flow line 38 and is pumped by a high-pressure pump 40 through the tubing string 28 into the portion of the well hole isolated by the upper and lower packers 24 and 26. The total input to the blender 34 is equal to the total output so that the fluid level in the blender 34 remains constant. Pressure from the fracturing fluid causes fractures 42 to form in the subsurface formation 14 and radiate outwardly from the perforations 18. Proppant which has been added to the slurry props open the fractures 42 to maintain channels within the subsurface formation 14 leading to the well 12.

The "clean" base fluid from the tank 30 passes by a suction flow-rate sensor 44 before entering the blender 34. The suction flow-rate sensor 44 is typically a turbine-like device in which the rotation of the turbine, caused by the fluid flow, is detected by a magnetic sensor which generates a series of pulses to be transmitted by a wire 46, processed and converted into a display, such as a digital suction flow-rate display 48. Similarly, the "dirty" proppant-laden slurry discharged from the blender through the discharge flow line 38 passes through a discharge flow rate sensor 50, which transmits a series of pulses through a wire 52 to be processed and displayed on a discharge flow-rate display 54. The suction and discharge flow rates, as displayed on the displays 48 and 54, are used by the operators to monitor the operation of the blender 34.

If used, a conventional nuclear densitometer (not shown) would be attached to the discharge flow line 38 between the blender 34 and the high-pressure pump 40 and would transmit a density signal to be displayed and used by the operators to monitor the amount of proppant in the fracturing fluid.

The present invention, however, employs the existing signals generated by the suction and discharge flow-rate sensors 44 and 50 to derive the density of the fluid discharged from the blender 34 relative to the density of the base fluid flowing into the blender 34 and display this information on a digital or other display 56 to be monitored by the operators. Additionally, an output of the densitometer 10 can be electrically interconnected by a cable 60 to a proppant control valve 62 as part of a closed-loop system to continuously and automatically regulate the amount of proppant in the slurry.

It has been found from empirical evaluations of suction and discharge flow rates and the amount of proppant added that, for a given amount of proppant, the ratio of the suction flow rate to the discharge flow rate is substantially constant. (Hereinafter, the relative density of the proppant-laden fluid will generally be referred to in units of "pounds of sands added" or "PSA"; it should be understood, however, that other units can also be used.) For example, given a PSA of ten, the suction:discharge ratio has been found to be about 0.686 when the discharge rate is 40 barrels per minute and also when it is 20 barrels per minute. Conversely, if the ratio is known, the PSA can be determined regardless of the suction and discharge flow rates. The present invention employs this relationship by determining the suction:discharge ratio and, based upon the ratio, calculating the amount of proppant added. This process is illustrated in the flow chart of FIG. 2. It will be appreciated that the method and apparatus of the present invention can be employed in any of a variety of applications and are not intended to be limited to use in the oil field service industry. Furthermore, the present invention can be implemented as an analog device or a digital device.

Tables 1 and 2 provide examples of the relationship between suction and discharge flow rates (as frequencies in Hz and as actual flow rates in barrels per minute) and the relative density of the slurry (in pounds of sand added). As can be seen, for any given S:D ratio, the PSA is the same whether the discharge rate is 20 barrels per minute or 40 barrels per minute. The PSA would also be the same for other discharge rates given the same S:D ratio.

TABLE 1

| Discharge Rate: 40 bls/min (82.8 Hz) | | | |
|---|---|---|---|
| Suction Rate (Hz) | Suction Rate (bls/min) | Ratio (S:D) | Density (PSA) |
| 79.16 | 38.24 | 0.956 | 1 |
| 75.85 | 36.64 | 0.916 | 2 |
| 72.78 | 35.16 | 0.879 | 3 |
| 69.97 | 33.80 | 0.845 | 4 |
| 67.40 | 32.56 | 0.814 | 5 |
| 65.00 | 31.40 | 0.785 | 6 |
| 62.76 | 30.32 | 0.758 | 7 |
| 60.61 | 29.28 | 0.732 | 8 |
| 58.71 | 28.36 | 0.709 | 9 |
| 56.80 | 27.44 | 0.686 | 10 |
| 55.06 | 26.60 | 0.665 | 11 |
| 53.49 | 25.84 | 0.646 | 12 |
| 51.92 | 25.08 | 0.627 | 13 |
| 50.51 | 24.40 | 0.610 | 14 |
| 49.10 | 23.72 | 0.593 | 15 |

TABLE 2

| Discharge Rate: 20 bls/min (41.4 Hz) | | | |
|---|---|---|---|
| Suction Rate (Hz) | Suction Rate (bls/min) | Ratio (S:D) | Density (PSA) |
| 39.58 | 19.12 | 0.956 | 1 |
| 37.92 | 18.32 | 0.916 | 2 |
| 36.39 | 17.58 | 0.879 | 3 |
| 34.98 | 16.90 | 0.845 | 4 |
| 33.70 | 16.28 | 0.814 | 5 |
| 32.50 | 15.70 | 0.785 | 6 |
| 31.38 | 15.16 | 0.758 | 7 |
| 30.31 | 14.64 | 0.732 | 8 |
| 29.35 | 14.18 | 0.709 | 9 |
| 28.40 | 13.72 | 0.686 | 10 |
| 27.53 | 13.30 | 0.665 | 11 |
| 26.74 | 12.92 | 0.646 | 12 |
| 25.96 | 12.54 | 0.627 | 13 |
| 25.25 | 12.20 | 0.610 | 14 |
| 24.55 | 11.86 | 0.593 | 15 |

Figure 2:
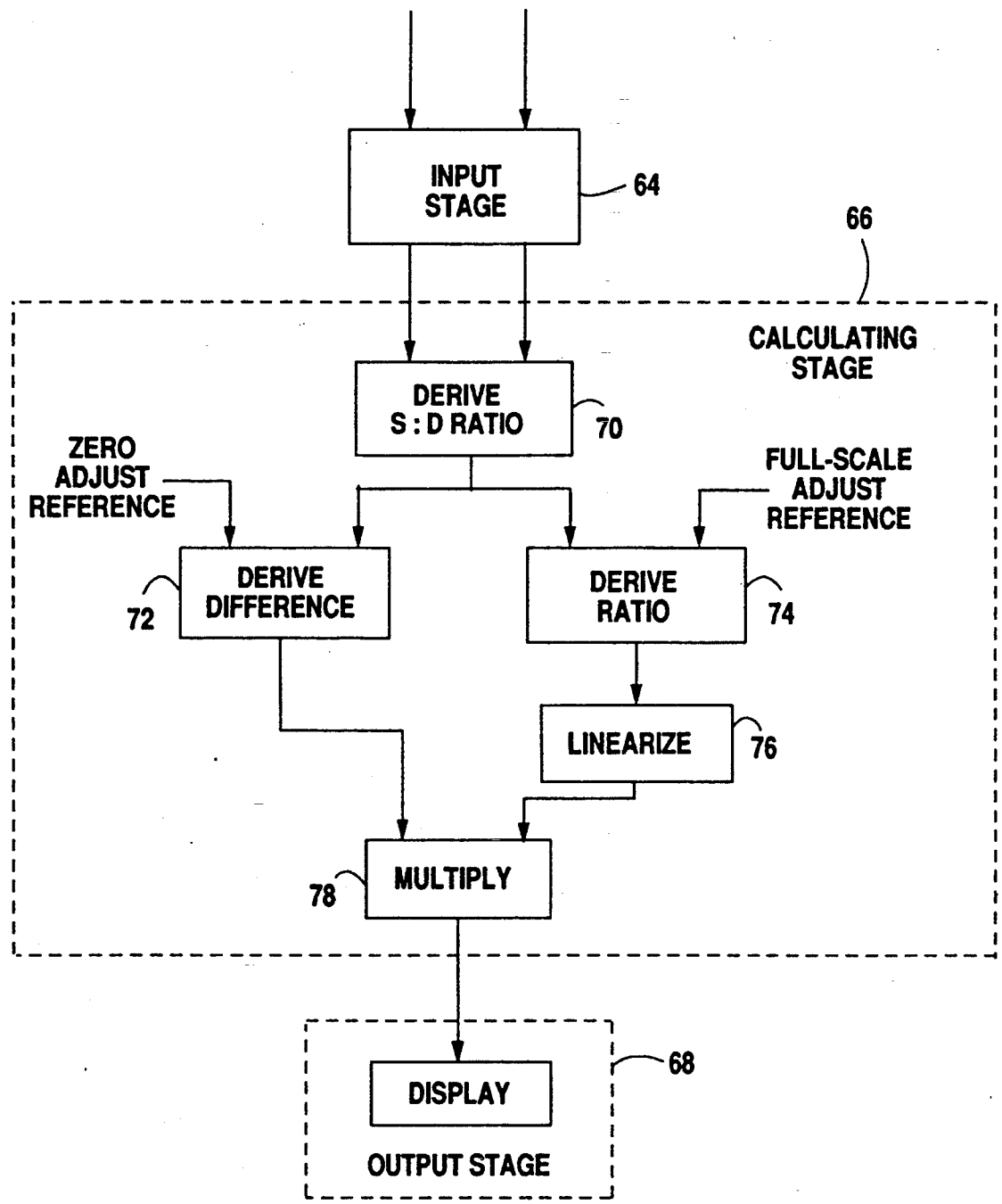
FIG. 2 illustrates a flow chart of an embodiment of the present invention.

Referring to FIG. 2, the densitometer 10 comprises an input stage 64 for generating two flow signals representative of the flow rates of the fluid flowing through the suction line 32 and through the discharge line 38, a calculating stage 66 for generating a density signal from the flow signals representative of the relative density of the fluid flowing through the discharge line 38, and an output stage 68 for indicating to the operators the density signal, such as with a visual display in appropriate units. In the calculating stage 66, the suction and discharge flow signals are received from the input stage 64, and their ratio, S:D, is derived 70. The S:D ratio is subtracted 72 from a zero adjustment reference to obtain a difference. The S:D ratio is also divided 74 into a full-scale adjustment reference to generate another ratio. Because the S:D ratio is not linear over the PSA range conventionally used in the stimulation services industry (from about 0 PSA to about 20 PSA), the second ratio is linearized 76 before the next step. The linearized second ratio is multiplied 78 by the difference of the zero adjustment reference minus the S:D ratio to generate the density signal.

Figure 3:
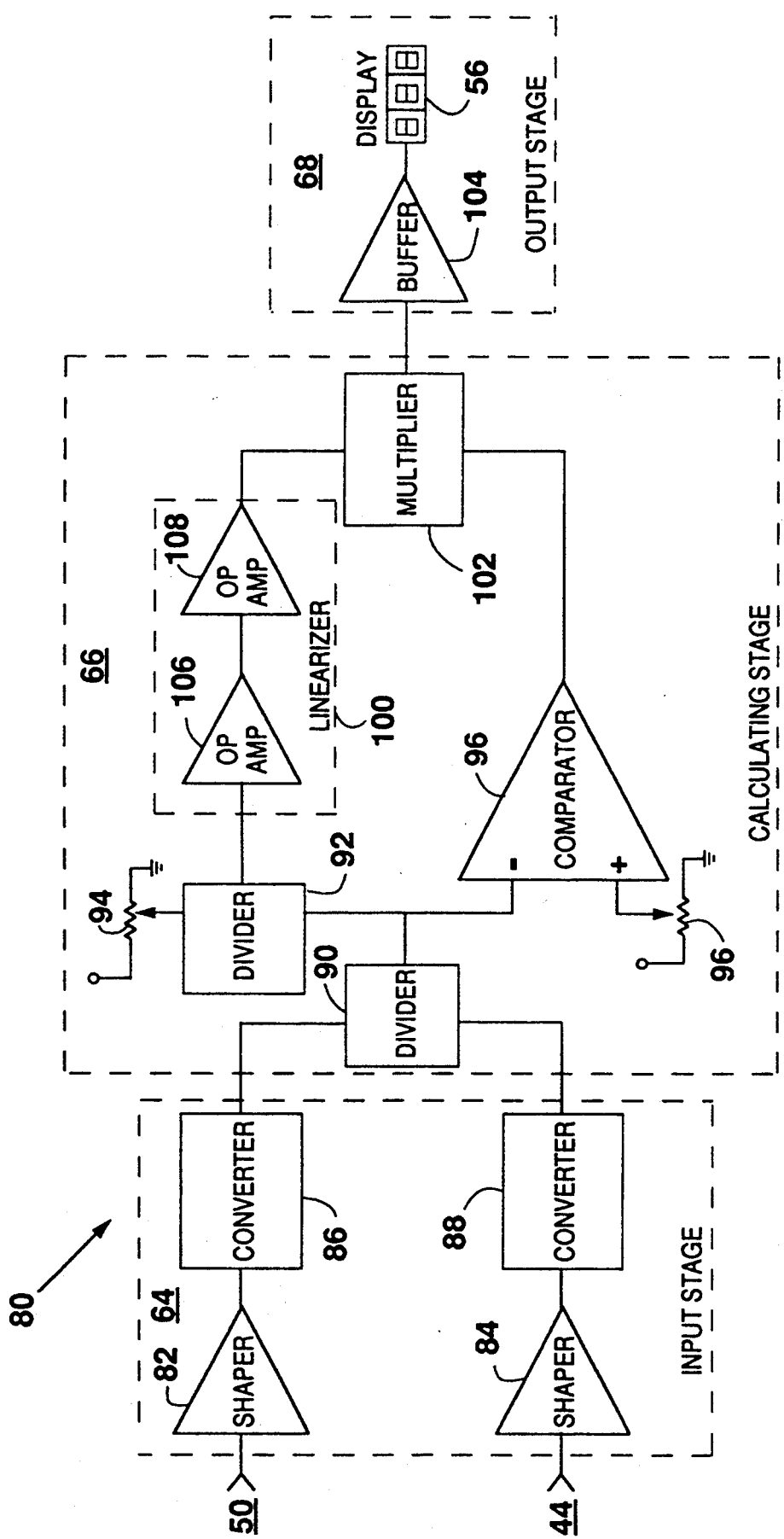
FIG. 3 illustrates a block diagram of an embodiment of the present invention in which the density signal is generated through analog circuitry.

FIG. 3 illustrates a block diagram of an analog embodiment of a densitometer 80 of the present invention, comprising the input stage 64, the calculating stage 66, and the output stage 68 described in conjunction with FIG. 2. The input stage 64 comprises a signal processor having a first input shaper 82 with an input electrically interconnected with the discharge flow-rate sensor 50 and a second input shaper 84 having an input electrically interconnected with the suction flow-rate sensor 44. Each of the input shapers 82 and 84 generates an output signal in the form of a substantially uniform series of square waves having the same frequency as the frequency of the input pulses from the flow-rate sensors 44 and 50. The input stage 64 also comprises first and second frequency-to-voltage converters 86 and 88, each of which generates an output voltage proportional to the frequency of the corresponding square waves. The two voltage flow signals from the converters 86 and 88 are transmitted to the calculating stage 66.

The calculating stage 66 includes a divider 90 which receives the two voltage signals from the input stage 64 and outputs a signal representing their ratio (i.e., suction flow rate divided by discharge flow rate). The output of the divider 90 is electrically interconnected with one input of a second divider 92; a second input of the divider 92 is electrically interconnected with a full-scale reference comprising a potentiometer 94 interconnected between a power supply and ground.

The output of the first divider 90 is also electrically interconnected with an inverting input of a comparator 96, the non-inverting input being interconnected with a zero adjustment reference, comprising a second potentiometer 98 interconnected between the power supply and ground.

The output of the second divider 92 is linearized in a linearizer 100 and is electrically interconnected with an input of a multiplier 102; the output of the comparator 96 is electrically interconnected with a second input of the multiplier 102. The output of the multiplier 102 is the density signal and is transmitted to the output stage 68. It can be displayed on the display 56 and, if desired, incorporated into a feedback loop (as illustrated in FIG. 1) to both monitor and control proppant density.

Various circuit components in the calculating stage 66 of the densitometer 80 cause the density signal output from the multiplier 102 to have a lower amplitude than is generally desired for satisfactory operation of the display 56. Consequently, the output stage 68 preferably includes a buffer 104 to amplify the density signal before it reaches the display 56. A range from about zero volts to about five volts is typically used to provide satisfactory resolution for a conventional three-digit LED display. Similarly, the linearizer 100 can comprise two inverting operational amplifiers 106 and 108 to increase the amplitude and linearity of the second ratio signal. By changing the gain of the buffer 104 and/or the linearizer 100, the densitometer 80 can be calibrated to display the density signal in any desired units.

The potentiometer 94 of the full-scale adjustment reference is preferably set only once, during factory calibration, to provide low-scale (e.g., 1 PSA) and full-scale (e.g., 15 PSA) readings on the display 56 when signals simulating appropriate flow rates are transmitted to the input stage 64.

The potentiometer 98 of the zero adjustment reference is field adjustable before each use of the densitometer 80. With the densitometer 80 connected to the suction and discharge flow-rate sensors 44 and 50, clean base fluid is pumped through the system and no proppant is added. Thus, the flow rates in the suction portion 32 and discharge portion 38 of the flow line will be the same (a ratio of one, indicating no proppant added), and the potentiometer 98 is adjusted until the display 56 reads zero PSA. This adjustment can compensate for minor variations in the flow rate sensors and turbines as well as changes in component values due to age and temperature variations.

Figure 4:
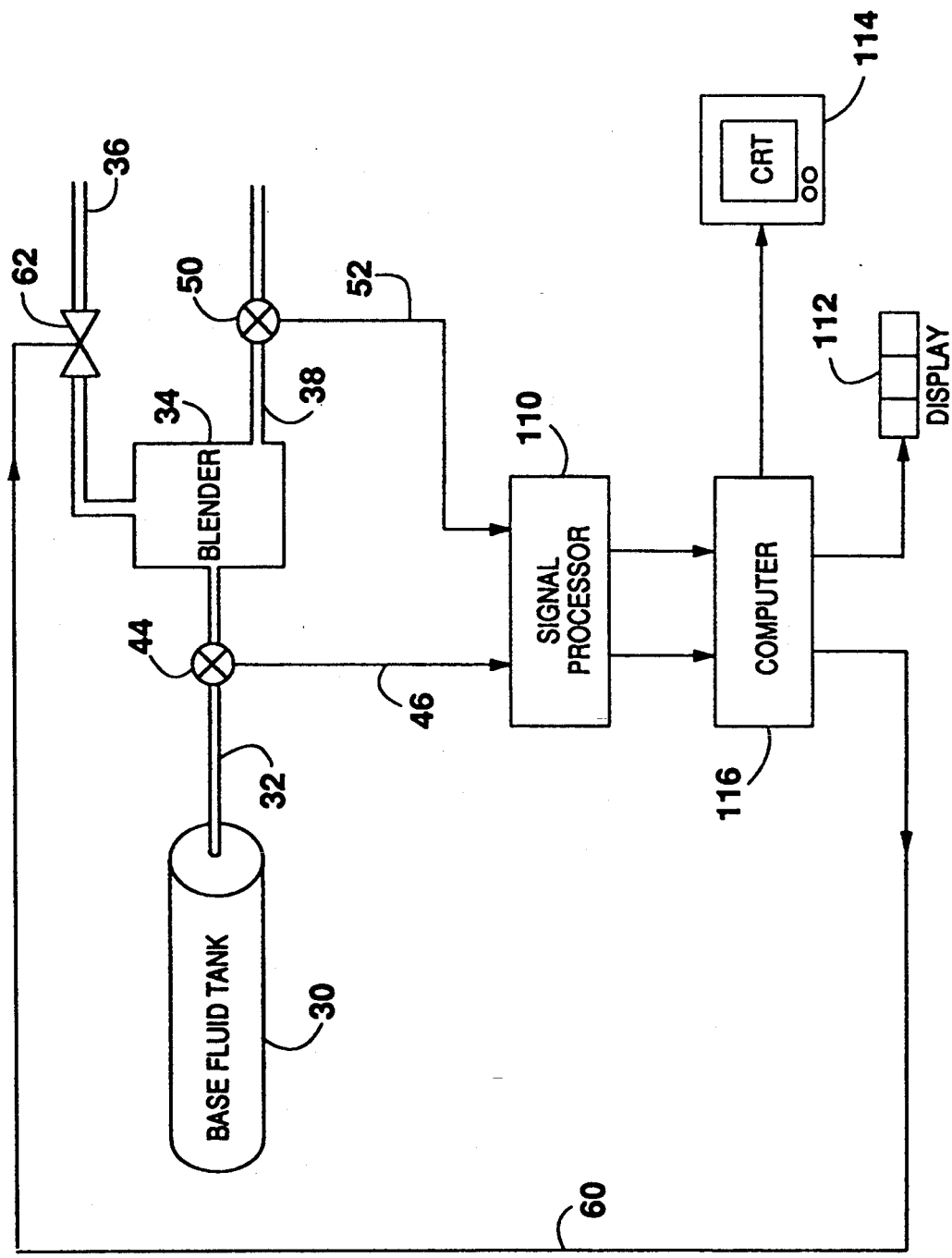
FIG. 4 schematically illustrates an embodiment of the present invention in which the density signal is generated by a digital computer.

FIG. 4 illustrates a densitometer in which the steps of the calculating stage 66, illustrated in FIG. 2, are implemented by a digital device, such as a computer 116. The signals from the suction and discharge flow rate sensors 44 and 50 are transmitted to a signal processor 110 which transmits digital flow signals to the computer 116. The computer 116 processes the signals and generates a density signal, which can be displayed on a digital display, such as LED display 112, on a CRT 114, or on both. The density signal can also be incorporated as part of a feedback loop and transmitted by the cable 60 to the valve 62 which controls the amount of proppant added to the blender 34. Thus, once a value for the desired amount of proppant has been entered into the computer 108, the system can maintain a relatively constant proppant density with significant speed and accuracy.

The signal processor 110 can be any means by which the signals from the flow rate sensors 44 and 50 are converted into appropriate digital signals for processing by the computer 108. For example, the input stage 110 can comprise circuitry similar to that of the input stage 64 of the embodiment illustrated in FIG. 3, including, for example, input shapers and frequency-to-voltage converters to generate uniform square waves to be processed by an analog-to-digital converter or processed directly by the computer 108.

The density signal can be calculated mathematically from the steps of FIG. 2 or can be obtained from a look-up table in memory based upon empirically derived data similar to that in Tables 1 and 2 above. If the density signal generated by the computer 108 is desired in analog form, a digital-to-analog converter can be employed for this purpose.

Although the present invention has been described in detail, it should be understood that various changes, substitutions, and alterations can be made herein without departing from the spirit and scope of the invention, as defined by the appended claims.

What is claimed is:

1. An apparatus for determining the amount of proppant in a flowing fracturing fluid, comprising:
   (a) an input stage, comprising:
      i) a first input for receiving a first input signal, having a first frequency, from a suction flow rate sensor representative of the flow rate of a fracturing fluid flowing through a first section of a flow line;
      ii) a second input for receiving a second input signal, having a second frequency, from a discharge flow rate sensor representative of the flow rate of the fracturing fluid flowing through a second section of the flow line after a proppant has been added to the fracturing fluid;
      iii) a first output for providing a first voltage signal proportional to said first frequency; and
      iv) a second output for providing a second voltage signal proportional to said second frequency;
   (b) first dividing means, having:
      i) a first input electrically interconnected with said first output of said input stage;
      ii) a second input electrically interconnected with said second output of said input stage; and
      iii) an output for providing a first ratio signal representative of said first voltage signal divided by said second voltage signal;
   (c) comparing means, having:
      i) a first input electrically interconnected with said output of said first dividing means;
      ii) a second input for receiving a first reference signal; and
      iii) an output for providing a difference signal representative of the difference between said first ratio signal and said first reference signal;
   (d) second dividing means, having:
      i) a first input electrically interconnected with said output of said first dividing means;
      ii) a second input for receiving a second reference signal; and
      iii) an output for providing a second ratio signal representative of said second reference signal divided by said first ratio signal; and
   (e) multiplying means, having:
      i) a first input electrically interconnected with said output of said comparing means;
      ii) a second input electrically interconnected with said output of said second dividing means; and
      iii) an output for providing a density signal substantially equal to the product of said difference signal times said second ratio signal and representative of the amount of proppant in the fracturing fluid flowing through the second section of flow line.

2. An apparatus as claimed in claim 1, wherein said input stage comprises:
   (a) a signal processor; and
   (b) a frequency-to-voltage converter.

3. An apparatus as claimed in claim 2, wherein said signal processor comprises:
   (a) a first input shaper to generate a first series of substantially square pulses; and
   (b) a second input shaper to generate a second series of substantially square pulses.

4. An apparatus as claimed in claim 3, comprising:
   (a) a first frequency-to-voltage circuit for converting said first series of substantially square pulses into said first voltage signal; and
   (b) a second frequency-to-voltage circuit for converting said second series of substantially square pulses into said second voltage signal.

5. An apparatus as claimed in claim 1, wherein said comparing means comprises a comparator wherein said first input of said comparing means is an inverting input of said comparator and said second input of said comparing means is a non-inverting input of said comparator.

6. An apparatus as claimed in claim 1, further comprising linearizer means having an input for receiving said second ratio signal and an output for providing a linearized second ratio signal being substantially linear over a predetermined range of first and second flow rates.

7. An apparatus as claimed in claim 6, wherein said linearizer means comprises an operational amplifier having:
   (a) an input electrically interconnected with said output of said second divider; and
   (b) an output electrically interconnected with said second input of said multiplier means.

8. An apparatus as claimed in claim 6, wherein said linearized second ratio signal has an amplitude from about 0 volts to about +5 volts.

9. An apparatus as claimed in claim 1, wherein:
   (a) said second reference is a voltage representative of one pound of sand added to the flowing fluid; and
   (b) said density signal has units of pounds of sand added.

10. An apparatus as claimed in claim 1, further comprising an operational amplifier having:
   (a) a non-inverting input electrically interconnected with said output of said multiplier; and
   (b) an output wherein said density signal is buffered by said operational amplifier.

11. An apparatus as claimed in claim 10, wherein said output of said operational amplifier has an amplitude from about 0 volts to about +5 volts.

12. An apparatus as claimed in claim 10, further comprising display means interconnected with said output of said operational amplifier for displaying said density signal.

13. An apparatus as claimed in claim 12, wherein said display means displays said density signal in units of pounds of sand added.

14. An apparatus for determining the relative density of a flowing fluid, comprising:
   (a) an input means for receiving flow rate information from a first and a second sections of a flow line and for generating first and second flow signals representative of flow rates of a fluid flowing through said first and second sections of said flow line;
   (b) a calculating means for generating a density signal from said first and second flow signals representative of the relative density of the fluid flowing through the second section of the flow line; and
   (c) an output means for displaying said density signal, wherein said input means comprise:
      a signal processor having:
         i) first means for converting a first input signal, representative of the flow rate of the fluid flowing through the first section of the flow line, into a first output signal having a first frequency; and
         ii) second means for converting a second input signal, representative of the flow rate of the fluid flowing through the second section of the flow line, into a second output signal having a second frequency; and
      (b) a frequency-to-voltage converter, having:
         i) first means for converting said first output signal into said first flow signal having an amplitude proportional to said first frequency; and
         ii) second means for converting said second output signal into said second flow signal having an amplitude proportional to said second frequency.

15. An apparatus as claimed in claim 14, wherein said signal processor further comprises:
   (a) a first input shaper to generate a first series of substantially square pulses; and
   (b) a second input shaper to generate a second series of substantially square pulses.

16. An apparatus as claimed in claim 14, comprising:
   (a) a first frequency-to-voltage circuit for converting said first series of substantially square pulses into a first voltage signal; and
   (b) a second frequency-to-voltage circuit for converting said second series of substantially square pulses into a second voltage signal.

17. An apparatus as claimed in claim 14, wherein said calculating means comprises:
   (a) means for deriving a first ratio representative of said first flow signal divided by said second flow signal;
   (b) means for deriving a difference between a first reference voltage and said first ratio;
   (c) means for deriving a second ratio representative of a second reference voltage divided by said first ratio; and
   (d) means for deriving a product of said second ratio times said difference.

18. An apparatus as claimed in claim 17, wherein said means for deriving a first ratio comprises a first dividing means, having:
   (a) a first input for receiving said first flow signal;
   (b) a second input for receiving said second flow signal; and
   (c) an output for providing a first ratio signal representative of said first flow signal divided by said second flow signal.

19. An apparatus as claimed in claim 18, wherein said means for deriving a difference comprises a comparing means, having:
   (a) a first input electrically interconnected with said output of said first dividing means;
   (b) a second input for receiving a first reference signal; and
   (c) an output for providing a difference signal representative of the difference between said first ratio signal and said first reference signal.

20. An apparatus as claimed in claim 19, wherein said means for deriving a second ratio comprises second dividing means, having:
   (a) a first input electrically interconnected with said output of said first dividing means;
   (b) a second input for receiving a second reference signal; and
   (c) an output for providing a second ratio signal representative of said second reference signal divided by said first ratio signal.

21. An apparatus as claimed in claim 20, wherein said means for deriving a product comprises multiplying means, having:
   (a) a first input electrically interconnected with said output of said comparing means;
   (b) a second input electrically interconnected with said output of said second dividing means; and
   (c) an output for providing said density signal substantially equal to the product of said difference signal times said second ratio signal and representative of the amount of proppant in the fracturing fluid flowing through the second section of flow line.

22. An apparatus as claimed in claim 17, further comprising linearizer means having:
   (a) an input for receiving said second ratio signal; and
   (b) an output for providing a linearized second ratio signal being substantially linear over a predetermined range of first and second flow rates.

23. An apparatus as claimed in claim 22, further comprising an output buffer having:
   (a) an input electrically interconnected with said output of said linearizer means; and
   (b) an output wherein said density signal has an amplitude from about 0 volts to about +5 volts.

24. An apparatus as claimed in claim 14, wherein said output means comprises a display means for displaying said density signal in units of pounds of sand added.

25. An apparatus as claimed in claim 24, wherein said display means displays said density signal in units of pounds of sand per gallon of fluid.

26. An apparatus as claimed in claim 24, wherein said display means displays said density signal in specific gravity units.

27. An apparatus as claimed in claim 14, wherein said input means comprises processing means for providing first and second digital flow signals representative of said first and second flow rates.

28. An apparatus as claimed in claim 27, wherein said processing means comprises an analog-to-digital converter for converting said first and second flow signals into said first and second digital flow signals.

29. An apparatus as claimed in claim 28, wherein said processing means further comprises:
(a) a signal processor having:
  i) first means for converting a first input signal, representative of the flow rate of the fluid flowing through the first section of the flow line, into a first output signal having a first frequency; and
  ii) second means for converting a second input signal, representative of the flow rate of the fluid flowing through the second section of the flow line, into a second output signal having a second frequency; and
(b) a frequency-to-voltage converter, having:
  i) first means for converting said first output signal into said first flow signal having an amplitude proportional to said first frequency; and p2 ii) second means for converting said second output signal into said second flow signal having an amplitude proportional to said second frequency, wherein first and second inputs of said analog-to-digital converter are electrically interconnected to said first and second outputs of said frequency-to-voltage converter.

30. An apparatus as claimed in claim 14, wherein said calculating means comprises a computer for generating said density signal from said first and second flow signals.

31. A method for determining the relative density of a flowing fluid, comprising the steps of:
(a) generating a first voltage representative of the flow rate of a fluid flowing through a first section of a flow line;
(b) generating a second voltage representative of the flow rate of the fluid flowing through a second section of the flow line;
(c) deriving a first ratio of the first voltage to the second voltage;
(d) comparing the first ratio to a first predetermined constant to derive a difference;
(e) deriving a second ratio of a second predetermined constant to the first ratio; and
(f) multiplying the difference by the second ratio to generate an output signal representative of the relative density of the fluid flowing through the second section of the flow line.

32. A method as claimed in claim 31, wherein:
(a) said step of generating the first voltage comprises the step of receiving a first input signal from a suction flow rate sensor, the first input signal having a first frequency; and
(b) said step of generating the second voltage comprises the step of receiving a second input signal from a discharge flow rate sensor, the second input signal having a second frequency.

33. A method as claimed in claim 32, wherein:
(a) said step of generating the first voltage further comprises the step of converting the first input signal into the first voltage having an amplitude substantially proportional to the first frequency; and
(b) said step of generating the second voltage further comprises the step of converting the second input signal into the second voltage having an amplitude substantially proportional to the second frequency.

34. A method as claimed in claim 31, wherein said step of deriving the first ratio comprises the step of dividing the first voltage by the second voltage.

35. A method as claimed in claim 31, wherein said step of deriving the second ratio comprises the step of dividing a reference voltage, having an amplitude substantially equal to the second predetermined constant, by the first ratio.

36. A method as claimed in claim 31, further comprising the step of displaying the output signal on a visual display.

37. A method as claimed in claim 31, further comprising the step of displaying the output signal on a visual display in units of pounds of sand added.

38. An apparatus for mixing a fracturing fluid with a proppant to obtain a mixture having a desired mixture density comprising:
mixing means for mixing said fracturing fluid with said proppant having an inlet line and a discharge line;
means for measuring a fracturing fluid flow rate in the inlet line;
means for adding granulated material to said fracturing fluid in said mixing means to form the mixture;
means for measuring a mixture flow rate in the discharge line;
means for calculating the density of the mixture based on the fracturing fluid and the mixture flow rates to obtain a calculated mixture density;
means for comparing the calculated mixture density with the desired mixture density to obtain a difference signal; and
means for controlling the fracturing fluid flow rate and the granulated material based on said difference signal.

* * * * *